(12) United States Patent
Müller et al.

(10) Patent No.: US 6,200,934 B1
(45) Date of Patent: Mar. 13, 2001

(54) SUBSTITUTED ARYLSULPHONYLAMINO(THIO)CARBONYL-TRIAZOLIN(THI)ONES AS HERBICIDES

(75) Inventors: Klaus-Helmut Müller, Düsseldorf; Mark Wilhelm Drewes, Langenfeld; Ernst Rudolf F. Gesing, Erkrath; Johannes Rudolf Jansen; Rolf Kirsten, both of Monheim; Joachim Kluth, Langenfeld; Klaus König, Odenthal; Hans-Jochem Riebel, Wuppertal; Otto Schallner, Monheim; Kurt Findeisen, Leverkusen, all of (DE); Markus Dollinger, Overland Park, KS (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/142,272

(22) PCT Filed: Feb. 24, 1997

(86) PCT No.: PCT/EP97/00878

§ 371 Date: Sep. 3, 1998

§ 102(e) Date: Sep. 3, 1998

(87) PCT Pub. No.: WO97/32876

PCT Pub. Date: Sep. 12, 1997

(30) Foreign Application Priority Data

Mar. 8, 1996 (DE) .............................................. 196 09 059

(51) Int. Cl.[7] ...................... A01N 43/653; C07D 249/14; C07D 249/12

(52) U.S. Cl. ................... 504/273; 548/263.2; 548/263.4; 548/263.8; 548/264.4; 548/264.6

(58) Field of Search .......................... 504/273; 548/263.2, 548/263.4, 263.8, 264.4, 264.6

(56) References Cited

U.S. PATENT DOCUMENTS 5,057,144 * 10/1991 Daum et al. .............................. 71/92
5,085,684 * 2/1992 Miller et al. .............................. 71/92

FOREIGN PATENT DOCUMENTS 0 341 489    11/1989   (EP) .

OTHER PUBLICATIONS

Cram and Hammond, "Organic Chemistry", Mc–Graw Hill Book Co., NY, (1964) 2nd ed., pp. 565–567.*

* cited by examiner

*Primary Examiner*—Patricia L. Morris
(74) *Attorney, Agent, or Firm*—Norris, McLaughlin & Marcus, P.A.

(57) ABSTRACT

The invention relates to novel substituted arylsulphonylamino(thio)carbonyl-triazolin(thi)ones of the formula (I)

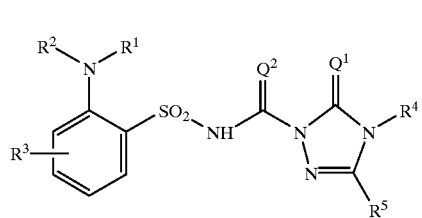

(I)

useful as herbicides.

4 Claims, No Drawings

SUBSTITUTED ARYLSULPHONYLAMINO (THIO)CARBONYL-TRIAZOLIN(THI)ONES AS HERBICIDES

The invention relates to novel substituted arylsulphonylamino(thio)carbonyl-triazolin(ethi)ones, to a plurality of processes for their preparation and to their use as herbicides.

It is already known that certain sulphonylaminocarbonyltriazolinones have herbicidal properties (cf. EP-A 341 489, EP-A 422 469, EP-A 425 948, EP-A 431 291, EP-A 507 171). However, the activity of these compounds is not in all aspects satisfactory.

This invention, accordingly, provides the novel substituted arylsulphonylamino(thio)carbonyl-triazolin(ethi)ones of the general formula (I)

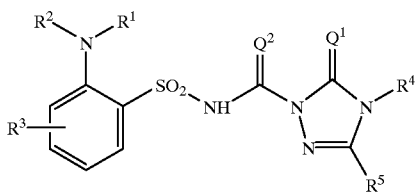

in which $Q^1$ represents oxygen or sulphur, $Q^2$ represents oxygen or sulphur, $R^1$ represents hydrogen, amino or represents respectively optionally substituted alkyl, alkoxy, alkylcarbonyl, alkoxycarbonyl, alkylthio, alkylsulphinyl, alkylsulphonyl, alkenyl, alkinyl or alkylideneamino, $R^2$ represents hydrogen or represents respectively optionally substituted alkyl, alkylcarbonyl, alkoxycarbonyl, alkylsulphonyl, alkenyl, or alkinyl, or together with $R^1$ represents alkanediyl which is optionally interrupted by oxygen and/or optionally substituted, $R^3$ represents hydrogen, cyano, nitro, halogen or represents respectively optionally substituted alkyl, alkylcarbonyl or alkoxycarbonyl, $R^4$ represents hydrogen, hydroxyl, amino, alkylideneamino or represents a respectively optionally substituted radical from the group alkyl, alkenyl, alkinyl, alkoxy, alkenyloxy, alkylamino, dialkylamino, cycloalkyl, cycloalkylalkyl, cycloalkylamino, aryl, arylalkyl, and $R^5$ represents hydrogen, hydroxyl, mercapto, amino, cyano, halogen or represents a respectively optionally substituted radical from the group alkyl, alkoxy, alkylthio, alkylamino, dialkylamino, alkenyl, alkinyl, alkenyloxy, alkinyloxy, alkenylthio, alkinylthio, alkenylamino, alkinylamino, cycloalkyl, cycloalkyloxy, cycloalkylthio, cycloalkylamino, cycloalkylalkyl, aryl, aryloxy, arylthio, arylamino, arylalkyl, and salts of compounds of the formula (I).

The novel substituted arylsulphonylamino(thio)carbonyl-triazolinones of the general formula (I) are obtained when (a) triazolin(ethi)ones of the general formula (II)

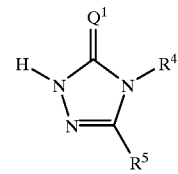

in which $Q^1$, $R^4$ and $R^5$ are each as defined above are reacted with sulphonyl iso(thio)cyanates of the general formula (III)

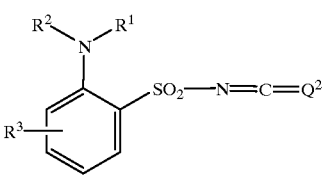

in which $Q^2$, $R^1$, $R^2$ and $R^3$ are each as defined above, if appropriate in the presence of a reaction auxiliary and if appropriate in the presence of a diluent, or when (b) triazolin(ethi)one derivatives of the general formula (IV)

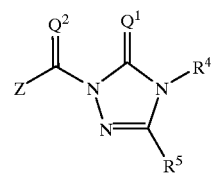

in which $Q^1$, $Q^2$, $R^4$ and $R^5$ are each as defined above and

Z represents halogen, alkoxy, aralkoxy or aryloxy, are reacted with sulphonamides of the general formula (V)

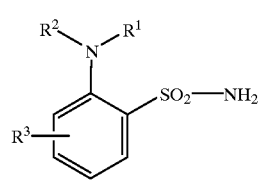

in which $R^1$, $R^2$ and $R^3$ are each as defined above, if appropriate in the presence of an acid acceptor and if appropriate in the presence of a diluent, or when
(c) triazolin(ethi)ones of the general formula (II)

$$\text{(II)}$$

in which
Q¹, R⁴ and R⁵ are each as defined above, are reacted with sulphonamide derivatives of the general formula (VI)

$$\text{(VI)}$$

in which
Q², R¹, R² and R³ are each as defined above and
Z represents halogen, alkoxy, aralkoxy or aryloxy,
if appropriate in the presence of an acid acceptor and if appropriate in the presence of a diluent,
or when
(d) triazolin(ethi)ones of the general formula (II)

$$\text{(II)}$$

in which
Q¹, R⁴ and R⁵ are each as defined above,
are reacted with sulphonyl halides of the general formula (VII)

$$\text{(VII)}$$

in which
R¹, R² and R³ are each as defined above and
X represents halogen,
and metal (thio)cyanates of the general formula (VIII)

$$MQ^2CN \quad \text{(VIII)}$$

in which
Q² is as defined above and
M represents an alkali metal or alkaline earth metal equivalent, if appropriate in the presence of a reaction auxiliary and if appropriate in the presence of a diluent,
and, if appropriate, the compounds of the formula (I) obtained by processes (a), (b), (c) or (d) are converted into salts by customary methods.

The novel substituted arylsulphonylamino(thio)carbonyltriazolinones of the general formula (I) have strong herbicidal activity.

The invention preferably provides compounds of the formula (I) in which
$Q^1$ represents oxygen or sulphur,
$Q^2$ represents oxygen or sulphur,
$R^1$ represents hydrogen, amino, represents respectively optionally cyano-, halogen- or $C_1$–$C_4$-alkoxy-substituted alkyl, alkoxy, alkylcarbonyl, alkoxycarbonyl, alkylthio, alkylsulphinyl or alkylsulphonyl having in each case 1 to 6 carbon atoms in the alkyl groups, or represents respectively optionally cyano- or halogen-substituted alkenyl, alkinyl or alkylideneamino having in each case 2 to 6 carbon atoms,
$R^2$ represents hydrogen, represents respectively optionally cyano-, halogen- or $C_1$–$C_4$-alkoxy-substituted alkyl, alkylcarbonyl, alkoxycarbonyl or alkylsulphonyl having in each case 1 to 6 carbon atoms in the alkyl groups, represents respectively optionally cyano- or halogen-substituted alkenyl or alkinyl having in each case 2 to 6 carbon atoms, or together with $R^1$ represents alkanediyl having 2 to 6 carbon atoms, which is optionally interrupted by oxygen and/or optionally substituted by halogen or $C_1$–$C_4$-alkyl,
$R^3$ represents hydrogen, cyano, nitro, halogen or represents respectively optionally halogen-substituted alkyl, alkylcarbonyl or alkoxycarbonyl having in each case 1 to 6 carbon atoms in the alkyl groups,
$R^4$ represents hydrogen, hydroxyl, amino, $C_1$–$C_6$-alkylideneamino, represents optionally fluorine-, chlorine-, bromine-, cyano-, $C_1$–$C_4$-alkoxy-, $C_1$–$C_4$-alkyl-carbonyl- or $C_1$–$C_4$-alkoxy-carbonyl-substituted $C_1$–$C_6$-alkyl, represents respectively optionally fluorine-, chlorine- and/or bromine-substituted $C_2$–$C_6$-alkenyl or $C_2$–$C_6$-alkinyl, represents $C_1$–$C_6$-alkyloxy or $C_3$–$C_6$-alkenyloxy, represents respectively optionally fluorine- and/or chlorine-substituted $C_1$–$C_6$-alkylamino, di-($C_1$–$C_4$-alkyl)-amino or $C_1$–$C_4$-alkanoylamino, represents respectively optionally fluorine-, chlorine-, bromine- and/or $C_1$–$C_4$-alkyl-substituted $C_3$–$C_6$-cycloalkyl or $C_3$–$C_6$-cycloalkyl-$C_1$–$C_4$-alkyl, or represents respectively optionally fluorine-, chlorine-, bromine-, cyano-, nitro-, $C_1$–$C_4$-alkyl-, trifluoromethyl-, $C_1$–$C_4$-alkoxy- and/or $C_1$–$C_4$-alkoxy-carbonyl-substituted phenyl or phenyl-$C_1$–$C_4$-alkyl, and
$R^5$ represents hydrogen, hydroxyl, mercapto, amino, cyano, halogen, represents respectively optionally cyano-, halogen- or $C_1$–$C_4$-alkoxy-substituted alkyl, alkoxy, alkylthio, alkylamino or dialkylamino having in each case 1 to 6 carbon atoms in the alkyl groups, represents respectively optionally cyano- or halogen-substituted alkenyl, alkinyl, alkenyloxy, alkinyloxy, alkenylthio, alkinylthio, alkenylamino or alkinylamino having in each case 2 to 6 carbon atoms, represents respectively optionally cyano-, halogen- or $C_1$–$C_4$-alkyl-substituted cycloalkyl, cycloalkyloxy, cycloalkylthio, cycloalkylamino or cycloalkyl-$C_1$–$C_4$-alkyl having in each case 3 to 6 carbon atoms in the cycloalkyl groups, or represents optionally cyano-, halogen-, $C_1$–$C_4$-alkyl-, $C_1$–$C_4$-halogenoalkyl, $C_1$–$C_4$-alkoxy- or $C_1$–$C_4$-halogenoalkoxy-substituted phenyl, phenoxy, phenylthio, phenylamino or phenyl-$C_1$–$C_4$-alkyl.

The invention furthermore preferably provides sodium, potassium, magnesium, calcium, ammonium, $C_1$–$C_4$-alkyl-ammonium, di-($C_1$–$C_4$-alkyl)-ammonium, tri-($C_1$–$C_4$-alkyl)-ammonium, tetra-($C_1$–$C_4$-alkyl)-ammonium, tri-($C_1$–$C_4$-alkyl)-sulphonium, $C_5$- or $C_6$-cycloalkyl-ammonium and di-($C_1$–$C_2$-alkyl)-benzyl-ammonium salts of compounds of the formula (I) in which $Q^1$, $Q^2$, $R^1$, $R^2$, $R^3$, $R^4$ and $R^5$ are each preferably as defined above.

The invention in particular provides compounds of the formula (I) in which $Q^1$ represents oxygen or sulphur, $Q^2$ represents oxygen or sulphur, $R^1$ represents hydrogen, represents respectively optionally cyano-, fluorine-, methoxy- or ethoxy-substituted methyl, ethyl, n- or i-propyl, n-, i-, s- or t-butyl, methoxy, ethoxy, n- or i-propoxy, acetyl, propionyl, n- or i-butyroyl, methoxycarbonyl, ethoxycarbonyl, n- or i-propoxycarbonyl, methylthio, ethylthio, n- or i-propylthio, methylsulphinyl, ethylsulphinyl, n- or i-propylsulphinyl, methylsulphonyl, ethylsulphonyl, n- or i-propylsulphonyl, represents propenyl, butenyl, propinyl or butinyl, or represents propylideneamino, $R^2$ represents hydrogen, represents respectively optionally cyano-, fluorine-, methoxy- or ethoxy-substituted methyl, ethyl, n- or i-propyl, n-, i-, s- or t-butyl, acetyl, propionyl, n- or i-butyroyl, represents methoxycarbonyl, ethoxycarbonyl, n- or i-propoxycarbonyl, methylsulphonyl, ethylsulphonyl, n- or i-propylsulphonyl, represents propenyl, butenyl, propinyl or butinyl, or together with $R^1$ represents respectively optionally methyl- and/or ethyl-substituted ethane-1,2-diyl, propane 1,3-diyl, butane-1,4-diyl, pentane-1,5-diyl or 3-oxa-pentane-1,5-diyl, $R^3$ represents hydrogen, represents cyano, nitro, fluorine, chlorine, bromine or represents respectively optionally fluorine-substituted methyl, ethyl, n- or i-propyl, $R^4$ represents hydrogen, represents respectively optionally fluorine-, chlorine-, cyano-, methoxy- or ethoxy-substituted methyl, ethyl, n- or i-propyl, n-, i-, s- or t-butyl, represents respectively optionally fluorine-, chlorine- or bromine-substituted propenyl, butenyl, propinyl or butinyl, represents methoxy, ethoxy, n- or i-propoxy or represents allyloxy, represents methylamino, ethylamino, n- or i-propylamino, n-, i-, s- or t-butylamino, dimethylamino or diethylamino, represents respectively optionally fluorine-, chlorine-, bromine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, or represents respectively optionally fluorine-, chlorine-, bromine-, cyano-, methyl-, trifluoromethyl- or methoxy-substituted benzyl or phenyl, and $R^5$ represents hydrogen, hydroxyl, mercapto, amino, fluorine, chlorine, bromine, represents respectively optionally fluorine-, chlorine-, cyano-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, represents respectively optionally cyano-, fluorine-, chlorine- or bromine-substituted propenyl, butenyl, propinyl, butinyl, propenyloxy, butenyloxy, propinyloxy, butinyloxy, propenylthio, butenylthio, propinylthio, butinylthio, propenylamino, butenylamino, propinylamino or butinylamino, represents respectively optionally cyano-, fluorine-, chlorine-, bromine-, methyl- or ethyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl or cyclohexylmethyl, or represents respectively optionally cyano-, fluorine-, chlorine-, methyl-, trifluoromethyl-, methoxy- or methoxycarbonyl-substituted phenyl, phenoxy, phenylthio, phenylamino or benzyl.

The abovementioned general or preferred radical definitions apply both to the end products of the formula (I) and, correspondingly, to the precursors or intermediates required in each case for the preparation. These radical definitions can be combined with one another as desired, thus including combinations between the preferred ranges indicated.

In the definitions of the radicals, hydrocarbon radicals such as alkyl, alkenyl or alkinyl are straight-chain or branched, including in combination with heteroatoms, as in alkoxy, alkylthio or alkylamino, even if this is not explicitly stated.

Halogen generally represents fluorine, chlorine, bromine or iodine, preferably fluorine, chlorine or bromine, in particular fluorine or chlorine.

Using, for example, 6-fluoro-2-(N-methyl-N-methylsulphonyl-amino)-phenylsulphonyl isocyanate and 4-ethyl-5-ethoxy-2,4-dihydro-3H-1,2,4-triazol-3-one as starting materials, the course of the reaction in the process (a) according to the invention can be illustrated by the following equation:

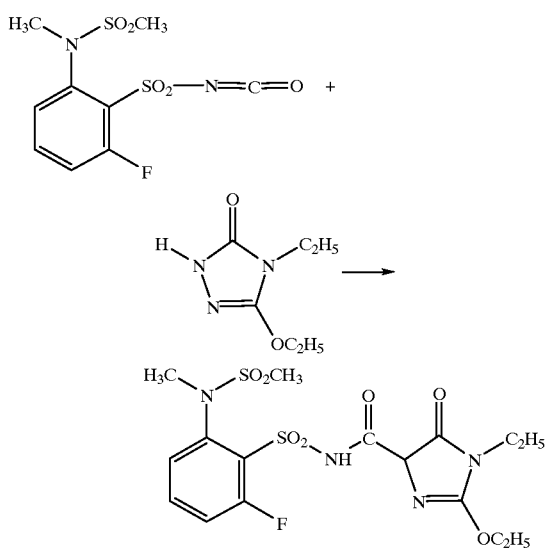

Using, for example, 2-ethylamino-benzenesulphonamide and 2-phenoxycarbonyl-4-methoxy-5-ethyl-2,4-dihydro-3H-1,2,4-triazol-3-one as starting materials, the course of the reaction in the process (b) according to the invention can be illustrated by the following equation:

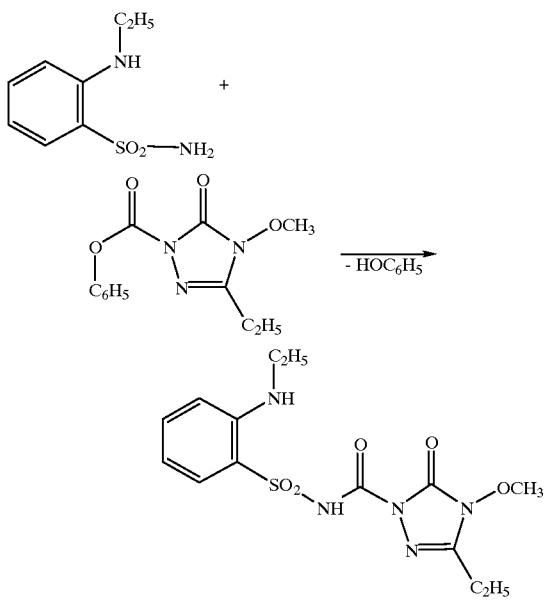

Using, for example, N-methoxycarbonyl-2-dimethylamino-3-methyl-benzene-sulphonamide and 4-methyl-5-methylthio-2,4-dihydro-3 H-1,2,4-triazol-3-one as starting materials, the course of the reaction in the process (c) according to the invention can be illustrated by the following equation:

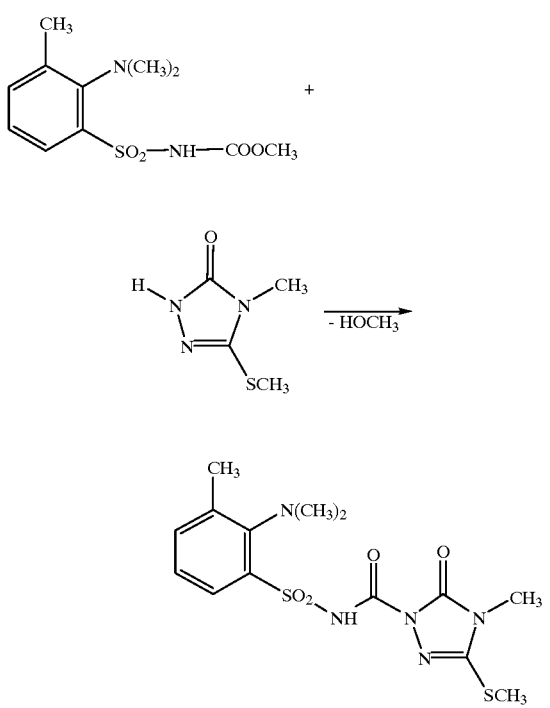

Using, for example, 2-allylamino-benzenesulphonyl chloride, 4-methylamino-5-methyl-2,4-dihydro-3H-1,2,4-triazol-3-one and sodium cyanate as starting materials, the course of the reaction in the process (d) according to the invention can be illustrated by the following equation:

The formula (II) provides a general definition of the traizolin(ethi)ones to be used as starting materials in the processes (a), (c) and (d) according to the invention for preparing compounds of the formula (1). In the formula (II), $Q^1$, $R^4$ and $R^5$ each preferably or in particular have those meanings which have already been indicated above, in connection with the description of the compounds of the formula (I) according to the invention, as being preferred or particularly preferred for $Q^1$, $R^4$ and $R^5$.

The triazolin(ethi)ones of the general formula (II) are known and/or can be prepared by processes known per se (cf. Arch. Pharm. 301 (1968), 827; loc. cit. 307 (1974), 889; Bull. Soc. Chim. France 1962, 1365; loc. cit. 1975, 1191; Chem. Ber. 90 (1957), 909–921; loc. cit. 98 (1965), 3025–3099; loc. cit. 102 (1969), 755; J. Heterocycl. Chem. 15 (1978), 237–240; J. Indian Chem. Soc. 6 (1929), 565; Liebigs Ann. Chem. 637 (1960), 135; Monatshefte Chemie 123 (1992), 257; Tetrahedron 32 (1976), 2347–2352; Helv. Chim. Acta 63 (1980), 841–859; J. Chem. Soc. C 1967, 746–751; loc. cit. 1970, 26–34; J. Chem. Soc. Perkin I 1973, 2644; Fen Fak. Derg., Seri A (Ege Univ.) 7 (1984), 1–6 - cited in Chem. Abstracts 101:90846m; EP-A 283 876; EP-A 294 666; EP-A 298 371; EP-A 301 946; EP-A 305 844; EP-A 341 489; EP-A 362 633; EP-A 370 293; EP-A 391 187; EP-A 398 096; EP-A 398 097; EP-A 399 294; EP-A 415 196; EP-A 422 469; EP-A 425 948; EP-A 431 291; EP-A 477 646; EP-A 502 307; EP-A 503 437; EP-A 505 819; EP-A 511 569; EP-A 513 621; DE-A 23 36 827; DE-A 38 39 206; DE-A 39 16 208; DE-A 39 16 930; DD-P 64 970; WO-A 93/04050).

The formula (III) provides a general definition of the sulphonyl iso(thio)cyanates further to be used as starting materials in the process (a) according to the invention for preparing compounds of the formula (I). In the formula (III), $Q^2$, $R^1$, $R^2$ and $R^3$ each preferably or in particular have those meanings which have already been indicated above, in connection with the description of the compounds of the formula (I) according to the invention, as being preferred or particularly preferred for $Q^2$, $R^1$, $R^2$ and $R^3$.

The starting materials of the formula (III) are known and/or can be prepared by processes known per se (cf. EP 385 775, DE 43 22 067, Preparation Examples).

The formula (IV) provides a general definition of the triazolin(ethi)one derivatives to be used as starting materials in the process (b) according to the invention for preparing the compounds of the general formula (I). In the formula (IV), $Q^1$, $Q^2$, $R^4$ and $R^3$ each preferably or in particular have those meanings which have already been indicated above, in connection with the description of the compounds of the formula (I), as being preferred or particularly preferred for $Q^1$, $Q^2$, $R^4$ and $R^5$; Z preferably represents fluorine, chlorine, bromine, methoxy, ethoxy, benzyloxy, phenoxy, halogeno- or nitro-phenoxy, in particular methoxy, phenoxy or 4-nitro-phenoxy.

The starting materials of the formula (IV) are known and/or can be prepared by processes known per se (cf. EP 341 489, EP 422 469, EP 425 948, EP 431 291, EP 507 171, EP 534 266).

The formula (V) provides a general definition of the sulphonamides further to be used as starting materials in the process (b) according to the invention for preparing the compounds of the general formula (I). In the formula (V), $R^1$, $R^2$ and $R^3$ each preferably or in particular have those meanings which have already been indicated above, in connection with the description of the compounds of the formula (I), as being preferred or particularly preferred for $R^1$, $R^2$ and $R^3$.

The starting materials of the formula (V) are known and/or can be prepared by processes known per se (cf. J. Med. Chem. 15 (1971), 432–439; J. Chem. Soc.; Perkin Trans. I 1974, 2451–2458; Justus Liebigs Ann. Chem. 1977, 1787–1798; Chem. Pharm. Bull. 27 (1979), 1287–1298; Synthesis 1981, 35–36; J: Med. Chem. 33 (1990), 1721–1728; EP 385 775; Preparation Examples).

The formula (VI) provides a general definition of the sulphonamide derivatives to be used as starting materials in the process (c) according to the invention for preparing the compounds of the formula (I). In the formula (VI), $Q^2$, $R^1$, $R^2$ and $R^3$ each preferably or in particular have those meanings which have already been indicated above, in connection with the description of the compounds of the formula (I), as being preferred or particularly preferred for $Q^2$, $R^1$, $R^2$ and $R^3$; Z preferably represents fluorine, chlorine, bromine, methoxy, ethoxy, benzyloxy or phenoxy, in particular methoxy or phenoxy.

The starting materials of the formula (VI) are known and/or can be prepared by processes known per se.

The formula (VII) provides a general definition of the sulphonyl halides to be used as starting materials in the process (d) according to the invention for preparing the compounds of the formula (I). In the formula (VII), $R^1$, $R^2$ and $R^3$ each preferably or in particular have those meanings which have already been indicated above, in connection with the description of the compounds of the formula (I), as being preferred or particularly preferred for $R^1$, $R^2$ and $R^3$; X preferably represents fluorine, chlorine or bromine, in particular chlorine.

The starting materials of the formula (VII) are known and/or can be prepared by processes known per se.

The processes (a), (b), (c) and (d) according to the invention for preparing the novel compounds of the formula (I) are preferably carried out using diluents. Suitable diluents are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene; ethers such as diethyl and dibutyl ether, glycol dimethyl ether and diglycol dimethyl ether, tetrahydrofuran and dioxane; ketones such as acetone, methyl ethyl, methyl isopropyl and methyl isobutyl ketone; esters such as methyl and ethyl acetate; nitriles such as, for example, acetonitrile and propionitrile; amides such as, for example, dimethylformamide, dimethylacetamide and N-methylpyrrolidone and also dimethyl sulphoxide, tetramethylene sulphone and hexamethylphosphoric triamide.

Suitable reaction auxiliaries or acid acceptors for the processes (a), (b), (c) and (d) according to the invention are all acid-binding agents which are customarily used for such reactions. Preference is given to alkali metal hydroxides such as, for example, sodium hydroxide and potassium hydroxide, alkaline earth metal hydroxides such as, for example, calcium hydroxide, alkali metal carbonates and alkoxides such as sodium carbonate and potassium carbonate, sodium tert-butoxide and potassium tert-butoxide, furthermore basic nitrogen compounds, such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo[4,3,0]-non-5-ene (DBN), 1,8-diazabicyclo [5,4,0]-undec-7-ene (DBU) and 1,4-diazabicyclo-[2,2,2]-octane (DABCO).

The reaction temperatures in the processes (a), (b), (c) and (d) according to the invention can be varied within a relatively wide range. The reactions are in general carried out at temperatures of between −20° C. and +100° C., preferably at temperatures between 0° C. and +80° C.

The processes (a), (b), (c) and (d) according to the invention are generally carried out under atmospheric pressure. However, it is also possible to operate under elevated or reduced pressure.

For carrying out processes (a), (b), (c) and (d) according to the invention, the starting materials required in each case are in general employed in approximately equimolar quantities. However, it is also possible to use one of the components employed in each case in a relatively large excess. The reactions are in general carried out in a suitable diluent in the presence of an acid acceptor, and the reaction mixture is stirred for a number of hours at the particular temperature required. Work-up in the case of the processes (a), (b), (c) and (d) according to the invention is in each case carried out by customary methods (cf. the Preparation Examples).

Salts of the compounds of the general formula (I) according to the invention can be prepared if desired. Such salts are obtained in a simple manner by customary methods of forming salts, for example by dissolving or dispersing a compound of the formula (I) in an appropriate solvent, for example methylene chloride, acetone, tert-butyl methyl ether or toluene, and adding an appropriate base. The salts can then—if desired after prolonged stirring—be isolated by concentration or filtration with suction.

The active compounds according to the invention can be used as defoliants, desiccants, haulm killers and, especially, as weed-killers. By weeds, in the broadest sense, are to be understood all plants which grow in locations where they are not wanted. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective control of weeds in annual crops.

The compounds of the formula (I) according to the invention are particularly suitable for the selective control of monocotyledonous and dicotyledonous weeds in monocotyledonous crops, both pre-emergence and post-emergence.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifying agents and/or dispersing agents and/or foam-forming agents.

If the extender used is water, it is also possible to use for example organic solvents as auxiliary solvents. Essentially, suitable liquid solvents are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are:
for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, and synthetic granules of inorganic and organic meals, and granules of organic material such as sawdust, coconut shells, maize cobs and tobacco stalks; suitable emulsifying and/or foam-forming agents are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersing agents are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general comprise between 0.1 and 95 per cent by weight of active compound, preferably between 0.5 and 90%.

For controlling weeds, the active compounds according to the invention, as such or in the form of their formulations, can also be used as mixtures with known herbicides, ready-to-use formulations or tank mixes being possible.

Possible components for the mixtures are known herbicides, for example anilides, such as diflufenican and propanil; arylcarboxylic acids, such as dichloropicolinic acid, dicamba and picloram; aryloxyalkanoic acids, such as 2,4-D, 2,4-DB, 2,4-DP, fluroxypyr, MCPA, MCPP and triclopyr; aryloxy-phenoxy-alkanoic esters, such as diclofop-methyl, fenoxaprop-ethyl, fluazifop-butyl, haloxyfop-methyl and quizalofop-ethyl; azinones, such as chloridazon and norflurazon; carbamates, such as chlorpropham, desmedipham, phenmedipham and propham; chloroacetanilides, such as alachlor, acetochlor, butachlor, metazachlor, metolachlor, pretilachlor and propachlor; dinitroanilines, such as oryzalin, pendimethalin and trifluralin; diphenyl ethers, such as acifluorfen, bifenox, fluoroglycofen, fomesafen, halosafen, lactofen and oxyfluorfen; ureas, such as chlorotoluron, diuron, fluometuron, isoproturon, linuron and methabenzthiazuron; hydroxylamines, such as alloxydim, clethodim, cycloxydim, sethoxydim and tralkoxydim; imidazolinones, such as imazethapyr, imazamethabenz, imazapyr and imazaquin; nitriles, such as bromoxynil, dichlobenil and ioxynil; oxyacetamides, such as mefenacet; sulfonylureas, such as amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates, such as butylate, cycloate, diallate, EPTC, esprocarb, molinate, prosulfocarb, thiobencarb and triallate; triazines, such as atrazine, cyanazine, simazine, simetryne, terbutryne and terbutylazine; triazinones, such as hexazinone, metamitron and metribuzin; others, such as aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulfosate and tridiphane.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 2 kg per ha.

The preparation and use of the active compounds according to the invention can be seen from the examples below.

PREPARATION EXAMPLES

Example 1

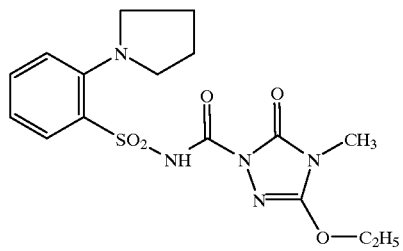

(Process (b))

3.4 g (15 mmol) of 2-pyrrolidino-benzenesulphonamide are initially charged in 100 ml of acetonitrile. 3.9 g (15 mmol) of 5-ethoxy-4-methyl-2-phenoxycarbonyl-2,4-dihydro-3H-1,2,4-triazol-3-one and then 1.7 g (15 mmol) of potassium t-butoxide are added, and the reaction mixture is subsequently stirred at room temperature (about 20° C.) for 15 hours. The mixture is then concentrated using waterpump vacuum and the residue is admixed with 50 ml of water. The mixture is acidified to pH 2 using conc. hydrochloric acid and then extracted twice with 50 ml of methylene chloride each time. The combined organic phases are dried using magnesium sulphate and then filtered. The filtrate is concentrated using waterpump vacuum, the residue is stirred with diethyl ether and the crystalline product is isolated by filtration with suction.

This gives 2.0 g (34% of theory) of 5-ethoxy-4-methyl-2-(2-pyrrolidino-phenyl-sulphonylaminocarbonyl)-2,4-dihydro-3H-1,2,4-triazol-3-one of melting point 68° C.

Example 2

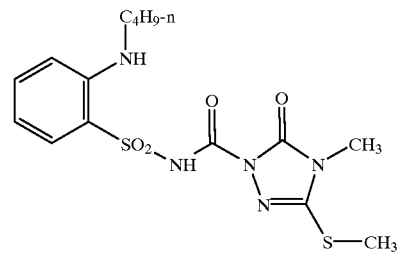

(Process (b))

1.4 g (6 mmol) of 2-n-butylamino-benzenesulphonamide are initially charged in 100 ml of acetonitrile and admixed with 1.6 g (6 mmol) of 4-methyl-5-methylthio-2-phenoxycarbonyl-2,4-dihydro-3H-1,2,4-triazol-3-one and 1.0 g (6.6 mmol) of diazabicycloundecene (DBU). The mixture is stirred at room temperature (about 20° C.) for 15 hours and subsequently concentrated using waterpump vacuum. The residue is admixed with water, adjusted to pH 1 using conc. hydrochloric acid and extracted twice with 50 ml of methylene chloride each time. The combined organic phases are washed with water, dried with magnesium sulphate and filtered. The filtrate is concentrated using waterpump vacuum, the residue is digested with diethyl ether and the crystalline product is isolated by filtration with suction.

This gives 0.8 g (34% of theory) of 2-(2-n-butylamino-phenylsulphonyl-aminocarbonyl)-4-methyl-5-methylthio-2,4-dihydro-3H-1,2,4-triazole-3-one of melting point 120° C.

Similarly to Examples 1 or 2, and in accordance with the general description of the preparation processes according to the invention, it is also possible to prepare, for example, the compounds of the formula (I) listed in Table 1 below.

TABLE 1

(I)

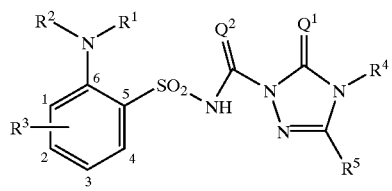

Examples of the compounds of the formula (I)

| Ex. No. | $Q^1$ | $Q^2$ | $R^1$ | (position-) $R^2$ | $R^3$ | $R^4$ | $R^5$ | Melting point (° C.) |
|---|---|---|---|---|---|---|---|---|
| 3 | O | O | H | H | (6-)CH$_3$ | CH$_3$ | OC$_2$H$_5$ | |
| 4 | O | O | H | —COCH$_3$ | H | CH$_3$ | OC$_2$H$_5$ | 140 |
| 5 | O | O | H | —COCH$_3$ | H | CH$_3$ | C$_2$H$_5$ | 120 |
| 6 | O | O | H | —COCH$_3$ | H | CH$_3$ | SCH$_3$ | 122 |

TABLE 1-continued

Examples of the compounds of the formula (I)

| Ex. No. | $Q^1$ | $Q^2$ | $R^1$ | $R^2$ | (position-) $R^3$ | $R^4$ | $R^5$ | Melting point (° C.) |
|---|---|---|---|---|---|---|---|---|
| 7 | O | O | —$COC_2H_5$ | —$COC_2H_5$ | H | $CH_3$ | $OC_2H_5$ | 120 |
| 8 | O | O | —$COC_2H_5$ | —$COC_2H_5$ | H | $CH_3$ | $C_2H_5$ | 98 |
| 9 | O | O | H | H | H | $CH_3$ | $SCH_3$ | 133 |
| 10 | O | O | H | H | H | $CH_3$ | $OC_2H_5$ | 142 |
| 11 | O | O | H | H | H | $CH_3$ | $C_2H_5$ | 190 |
| 12 | O | O | H | H | (5-)Br | $CH_3$ | $OC_2H_5$ | 127 |
| 13 | O | O |  | —$(CH_2)_4$— | H | $CH_3$ | $SCH_3$ | 120 |
| 14 | O | O |  | —$(CH_2)_4$— | H | $CH_3$ | $C_2H_5$ | 102 |
| 15 | O | O |  | —$(CH_2)_4$— | (5-)$NO_2$ | $CH_3$ | $SCH_3$ | 157 |
| 16 | O | O |  | —$(CH_2)_4$— | (5-)$NO_2$ | $CH_3$ | $OC_2H_5$ | 156 |
| 17 | O | O |  | —$(CH_2)_4$— | (5-)$NO_2$ | $CH_3$ | $C_2H_5$ | 138 |
| 18 | O | O |  | —$(CH_2)_4$— | (5-)$NO_2$ | $CH_3$ | $CH_2OCH_3$ | 150 |
| 19 | O | O |  | —$(CH_2)_4$— | (5-)$NO_2$ | $CH_3$ | $SC_2H_5$ | 125 |
| 20 | O | O |  | —$(CH_2)_4$— | (5-)$NO_2$ | $CH_3$ | n-$C_3H_7$ | 160 |
| 21 | O | O |  | —$(CH_2)_2$—O—$(CH_2)_2$— | H | $CH_3$ | $SCH_3$ | 156 |
| 22 | O | O |  | —$(CH_2)_2$—O—$(CH_2)_2$— | H | $CH_3$ | $C_2H_5$ | 158 |
| 23 | O | O |  | —$(CH_2)_2$—O—$(CH_2)_2$— | H | $CH_3$ | $OC_2H_5$ | 192 |
| 24 | O | O |  | —$(CH_2)_2$—O—$(CH_2)_2$— | (5-)$NO_2$ | $CH_3$ | $SCH_3$ | 172 |
| 25 | O | O |  | —$(CH_2)_2$—O—$(CH_2)_2$— | H | $CH_3$ | n-$C_3H_7$ | 182 |
| 26 | O | O |  | —$(CH_2)_2$—O—$(CH_2)_2$— | H | $CH_3$ | $SC_2H_5$ | 122 |
| 27 | O | O | $C_2H_5$ | $C_2H_5$ | (5-)$NO_2$ | $CH_3$ | $SCH_3$ | 165 |
| 28 | O | O | $C_2H_5$ | $C_2H_5$ | (5-)$NO_2$ | $CH_3$ | $SC_2H_5$ | 178 |
| 29 | O | O |  | —$(CH_2)_2$—O—$(CH_2)_2$— | (5-)$NO_2$ | $CH_3$ | $CH_3$ | 120 |
| 30 | O | O |  | —$(CH_2)_2$—O—$(CH_2)_2$— | (5-)$NO_2$ | $CH_3$ | $SC_2H_5$ | 145 |
| 31 | O | O |  | —$(CH_2)_2$—O—$(CH_2)_2$— | (5-)$NO_2$ | $CH_3$ | $C_2H_5$ | 160 |
| 32 | O | O |  | —$(CH_2)_2$—O—$(CH_2)_2$— | (5-)$NO_2$ | $CH_3$ | $OC_2H_5$ | 100 |
| 33 | O | O | H | n-$C_3H_7$ | (5-)$NO_2$ | $CH_3$ | $SCH_3$ | 120 |
| 34 | O | O | H | n-$C_3H_7$ | (5-)$NO_2$ | $CH_3$ | $OC_2H_5$ | 127 |
| 35 | O | O | H | —$CH_2CH_2OCH_3$ | H | $CH_3$ | $OC_2H_5$ | 182 |
| 36 | O | O | H | —$CH_2CH_2OCH_3$ | H | $CH_3$ | $C_2H_5$ | 140 |
| 37 | O | O | H | —$CH_2CH_2OC_2H_5$ | H | $CH_3$ | $OC_2H_5$ | 155 |
| 38 | O | O | H | $(CH_3)_2C=N$— | H | (5-)$NO_2$ | $CH_3$ | $OC_2H_5$ | 140 |
| 39 | O | O | H | n-$C_3H_7$ | (5-)$NO_2$ | $CH_3$ | $C_2H_5$ | 105 |
| 40 | O | O | $NH_2$ | $CH_3$ | (5-)$NO_2$ | $CH_3$ | $OC_2H_5$ | 208 |

TABLE 1-continued

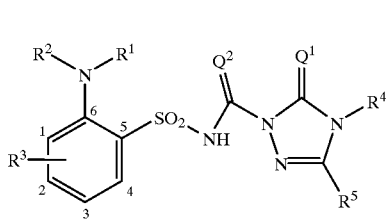

Examples of the compounds of the formula (I)

| Ex. No. | Q¹ | Q² | R¹ | R² (position-) | R³ | R⁴ | R⁵ | Melting point (° C.) |
|---|---|---|---|---|---|---|---|---|
| 41 | O | O | H | -CH₂CH₂-O-C₂H₅ | (5-)NO₂ | CH₃ | C₂H₅ | 90 |
| 42 | O | O | H | C₂H₅ | H | CH₃ | OCH₃ | 112 |
| 43 | O | O | H | C₂H₅ | H | CH₃ | C₂H₅ | 125 |
| 44 | O | O | H | C₂H₅ | H | CH₃ | OC₃H₇-i | 80 |
| 45 | O | O | H | C₂H₅ | H | cyclopropyl | OC₂H₅ | 108 |
| 46 | O | S | H | C₂H₅ | H | OC₂H₅ | C₂H₅ | 85 |
| 47 | O | S | H | C₂H₅ | H | CH₃ | CH₂OCH₃ | 110 |
| 48 | O | S | H | C₂H₅ | H | cyclopropyl | Br | 105 |
| 49 | O | O | H | i-C₃H₇ | H | CH₃ | C₂H₅ | 103 |
| 50 | O | O | H | i-C₃H₇ | H | CH₃ | OC₂H₅ | 88 |
| 51 | O | O | H | i-C₃H₇ | H | CH₃ | SCH₃ | 108 |
| 52 | O | S | H | i-C₃H₇ | H | CH₃ | SO₂CH₃ | 157 |
| 53 | O | S | H | i-C₃H₇ | H | cyclopropyl | Br | 127 |
| 54 | O | O | H | -CH₂-CH=CH₂ | H | CH₃ | SCH₃ | 115 |
| 55 | O | O | H | n-C₄H₉ | H | CH₃ | OC₂H₅ | 118 |
| 56 | O | O | H | n-C₄H₉ | H | CH₃ | C₂H₅ | 75 |
| 57 | O | S | H | n-C₄H₉ | H | cyclopropyl | Br | 110 |
| 58 | O | O | H | —COCH₃ | (5-)Cl | CH₃ | SCH₃ | 158 |
| 59 | O | O | H | CH₃ | H | CH₃ | SCH₃ | 167 |
| 60 | O | O | H | CH₃ | H | CH₃ | OC₂H₅ | 156 |
| 61 | O | O | H | CH₃ | H | CH₃ | C₂H₅ | 175 |
| 62 | O | O | H | H | (5-)CH₃ | CH₃ | OC₂H₅ | 143 |
| 63 | O | O | H | H | (5-)CH₃ | CH₃ | SCH₃ | 225 |
| 64 | O | O | H | H | (5-)CH₃ | CH₃ | C₂H₅ | 183 |
| 65 | O | O | H | H | (5-)Cl | CH₃ | SCH₃ | 150 |
| 66 | O | O | H | H | (5-)Cl | CH₃ | C₂H₅ | 150 |
| 67 | O | O | H | H | H | CH₃ | SCH₃ | |

TABLE 1-continued

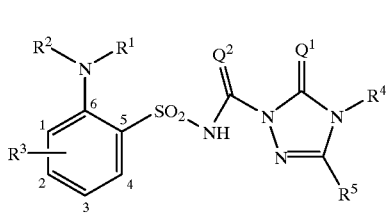

Examples of the compounds of the formula (I)

| Ex. No. | $Q^1$ | $Q^2$ | $R^1$ | $R^2$ | $R^3$ | $R^4$ | $R^5$ | Melting point (° C.) |
|---|---|---|---|---|---|---|---|---|
| 68 | O | O | H | $C_2H_5$ | H | $CH_3$ | $OC_2H_5$ | (K salt) 132 |
| 69 | O | O | H | $C_2H_5$ | H | $CH_3$ | $SCH_3$ | 153 |
| 70 | O | O | H | H | (6-)Cl | $CH_3$ | $C_2H_5$ | 208 |
| 71 | O | O | H | H | (6-)Cl | $CH_3$ | $OCH_3$ | 202 |
| 72 | O | O | H | H | (6-)$CH_3$ | $CH_3$ | $SCH_3$ | 198 |

Starting materials of the formula (V):

Example (V-1)

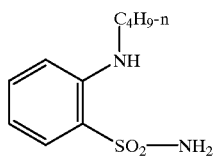

Step 1:

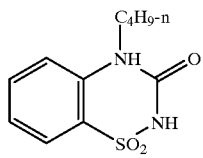

56 ml of chlorosulphonyl isocyanate are initially charged in 250 ml of nitromethane and cooled to −10° C. 93.7 g (0.63 mol) of N-butyl-aniline are then added dropwise, while the internal temperature is maintained at −10° C. The mixture is stirred at −10° C. for about 30 minutes. At about +15° C., 93 g (0.7 mol) of aluminium trichloride are then added a little at a time, while cooling with an icebath. The mixture is subsequently poured onto ice-water and adjusted to pH 1 using conc. hydrochloric acid. The crystalline product is isolated by filtration with suction.

This gives 102 g (64% of theory) of 4-n-butyl-1,2,3,4-tetrahydro-1,2,4-benzothiadiazin-3-one 1,1-dioxide.

Step 2:

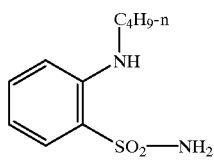

102 g (0.04 mol) of 4-n-butyl-1,2,3,4-tetrahydro-1,2,4-benzothiadiazin-3-one 1,1-dioxide are mixed with 500 ml of 50% strength sulphuric acid, and the mixture is heated under reflux until a clear solution is obtained. The mixture is cooled to room temperature (about 20° C.), poured into water and neutralized using conc. aqueous sodium hydroxide solution. The crystalline product is isolated by filtration with suction and dewatered azeotropically using toluene.

This gives 55.1 g (60% of theory) of 2-n-butylamino-benzenesulphonamide.

Example (V-2)

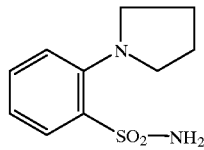

A mixture of 28.2 g (0.16 mol) of 2-fluoro-benzenesulphonamide and 32 g (0.45 mol) of pyrrolidine is heated under reflux for three hours. The mixture is subsequently concentrated using waterpump vacuum and the residue is stirred with 200 ml of water for about 15 hours. 10 ml of conc. hydrochloric acid are then added and the crystalline product is isolated by filtration with suction.

This gives 20.7 g (61% of theory) of 2-pyrrolidino-benzenesulphonamide of melting point 78° C.

Use Examples

Example A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After 24 hours, this soil is sprayed with the preparation of active compound. It is advantageous to keep the amount of water per unit area constant. The concentration of active compound in the preparation is of no importance, only the amount of active compound per unit area is decisive.

After three weeks, the degree of damage to the plants is rated in % damage in comparison with the development of the untreated control.

The figures denote:
0%=no effect (like untreated control)
100%=total destruction In this test, the compounds according to the invention of Preparation Example 3, 23, 49, 50, 60 and 68, for example, exhibit strong activity against weeds (cf. Tables A-1 to A-5), and some are tolerated well by crop plants, such as wheat and maize. "ai."="active ingredient"

unit area. The concentration of the spray liquor is chosen so that the particular amounts of active compound desired are applied in 1000 l of water/ha.

After three weeks, the degree of damage to the plants is rated in % damage in comparison with the development of the untreated control.

The figures denote:
0%=no effect (like untreated control)
100%=total destruction In this test, the compound according to the invention of Preparation Example 71, for example, exhibits strong activity against weeds (cf. Table B).

TABLE A

Pre-emergence test/greenhouse

Table A-1

| Compound of Preparation Ex. No. | Application rate (g of ai./ha) | Wheat | Cotton | Alopecurus | Cyperus | Poa | Matricaria |
|---|---|---|---|---|---|---|---|
| (3) | 60 | 0 | 0 | 95 | 80 | 80 | 80 |

Table A-2

| Compound of Preparation Ex. No. | Application rate (g of ai./ha) | Wheat | Soya | Cyperus | Setaria | Solanum | Xanthium |
|---|---|---|---|---|---|---|---|
| (23) | 125 | 20 | 0 | 90 | 80 | 80 | 90 |

Table A-3

| Compound of Preparation Ex. No. | Application rate (g of ai./ha) | Wheat | Cotton | Sunflowers | Alopecurus | Echinochloa | Amaranthus | Chenopodium |
|---|---|---|---|---|---|---|---|---|
| (50) | 125 | 0 | 20 | — | 95 | 80 | 80 | 95 |
| (60) | 250 | 20 | — | 20 | 80 | 80 | 95 | 80 |

Table A-4

| Compound of Preparation Ex. No. | Application rate (g of ai./ha) | Maize | Cotton | Alopecurus | Galium | Matricaria |
|---|---|---|---|---|---|---|
| (49) | 125 | 0 | 0 | 90 | 90 | 95 |
| (50) | 125 | 0 | 20 | 95 | 95 | 90 |

Table A-5

| Compound of Preparation Ex. No. | Application rate (g of ai./ha) | Alopecurus | Setaria | Amaranthus | Galinsoga | Sinapis |
|---|---|---|---|---|---|---|
| (68) | 125 | 95 | 95 | 95 | 95 | 95 |

Example B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of active compound in such a way as to apply the particular amounts of active compound desired per

TABLE B

Post-emergence test/greenhouse

| Compound of Preparation Ex. No. | Application rate (g of ai./ha) | Wheat | Sunflowers | Avena | Sorghum | Amaranthus | Solanum |
|---|---|---|---|---|---|---|---|
| (71) | 125 | 10 | 10 | 80 | 80 | 90 | 90 |

What is claimed is:

1. A compound of the formula (I)

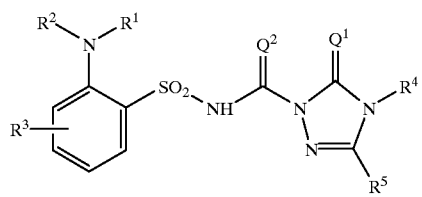

in which $Q^1$ represents oxygen or sulphur, $Q^2$ represents oxygen or sulphur, $R^1$ represents hydrogen, amino, represents respectively optionally cyano-, halogen- or $C_1$–$C_4$-alkoxy-substituted alkyl, alkoxy, alkylcarbonyl, alkoxycarbonyl, alkylthio, alkylsulphinyl or alkylsulphonyl having in each case 1 to 6 carbon atoms in the alkyl groups, or represents respectively optionally cyano- or halogen-substituted alkenyl, alkinyl or alkylideneamino having in each case 2 to 6 carbon atoms, $R^2$ represents hydrogen, represents respectively optionally cyano-, halogen- or $C_1$–$C_4$-alkoxy-substituted alkyl, alkylcarbonyl, alkoxycarbonyl or alkylsulphonyl having in each case 1 to 6 carbon atoms in the alkyl groups, represents respectively optionally cyano- or halogen-substituted alkenyl or alkinyl having in each case 2 to 6 carbon atoms, $R^3$ represents hydrogen, cyano, nitro, halogen or represents respectively optionally halogen-substituted alkyl, alkylcarbonyl or alkoxycarbonyl having in each case 1 to 6 carbon atoms in the alkyl groups, $R^4$ represents hydrogen, hydroxyl, amino, $C_1$–$C_6$-alkylideneamino, represents optionally fluorine-, chlorine-, bromine-, cyano-, $C_1$–$C_4$-alkoxy-, $C_1$–$C_4$-alkyl-carbonyl- or $C_1$–$C_4$-alkoxy-carbonyl-substituted $C_1$–$C_6$-alkyl, represents respectively optionally fluorine-, chlorine- and/or bromine-substituted $C_2$–$C_6$-alkenyl or $C_2$–$C_6$-alkinyl, represents $C_1$–$C_6$-alkyloxy or $C_3$–$C_6$-alkenyloxy, represents respectively optionally fluorine- and/or chlorine-substituted $C_1$–$C_6$-alkylamino, di-(C-$C_4$-alkyl)-amino or $C_1$–$C_4$-alkanoylamino, represents respectively optionally fluorine-, chlorine-, bromine- and/or $C_1$–$C_4$-substituted C3–$C_6$-cycloalkyl or $C_3$–$C_6$-cycloalkyl-$C_1$–$C_4$-alkyl, or represents respectively optionally fluorine-, chlorine-, bromine-, cyano-, nitro-, $C_1$–$C_4$-alkyl-, trifluoromethyl-, $C_1$–$C_4$-alkoxy- and/or $C_1$–C4-alkoxy carbonyl-substituted phenyl or phenyl-$C_1$–$C_4$-alkyl, and $R^5$ represents hydrogen, hydroxyl, mercapto, amino, cyano, halogen, represents respectively optionally cyano-, halogen- or $C_1$–$C_4$-alkoxy-substituted alkyl, alkoxy, alkylthio, alkylamino or dialkylamino having in each case 1 to 6 carbon atoms in the alkyl groups, represents respectively optionally cyano- or halogen-substituted alkenyl, alkinyl, alkenyloxy, alkinyloxy, alkenylthio, alkinylthio, alkenylamino or alkinylamino having in each case 2 to 6 carbon atoms, represents respectively optionally cyano-, halogen- or $C_1$–$C_4$-alkyl-substituted cycloalkyl, cycloalkyloxy, cycloalkylthio, cycloalkylamino or cycloalkyl-$C_1$–$C_4$-alkyl having in each case 3 to 6 carbon atoms in the cycloalkyl groups, or represents optionally cyano-, halogen-, $C_1$–$C_4$-alkyl-, $C_1$–$C_4$-halogenoalkyl, $C_1$–$C_4$-alkoxy- or $C_1$–$C_4$-halogenoalkoxy-substituted phenyl, phenoxy, phenylthio, phenylamino or phenyl-$C_1$–$C_4$-alkyl, and the sodium, potassium, magnesium, calcium, ammonium, $C_1$–$C_4$-alkyl-ammonium, di-($C_1$–$C_4$-alkyl)-ammonium, tri-($C_1$–$C_4$-alkyl)-ammonium, tetra-($C_1$–$C_4$-alkyl)-ammonium, tri-($C_1$–$C_4$-alkyl)-sulphonium, $C_5$- or $C_6$-cycloalkyl-ammonium and di-($C_1$–$C_2$-alkyl)-benzyl-ammonium salt[s] of compound[s] of the formula (I).

2. A compound of the formula (I) according to claim 1, in which $Q^1$ represents oxygen or sulphur, $Q^2$ represents oxygen or sulphur, $R^1$ represents hydrogen, represents respectively optionally cyano-, fluorine-, methoxy- or ethoxy-substituted methyl, ethyl, n- or i-propyl, n-, i-, s- or t-butyl, methoxy, ethoxy, n- or i-propoxy, acetyl, propionyl, n- or i-butyroyl, methoxycarbonyl, ethoxycarbonyl, n- or i-propoxycarbonyl, methylthio, ethylthio, n- or i-propylthio, methylsulphinyl, ethylsulphinyl, n- or i-propylsulphinyl, methylsulphonyl, ethylsulphonyl, n- or i-propylsulphonyl, represents propenyl, butenyl, propinyl or butinyl, or represents propylideneamino, $R^2$ represents hydrogen, represents respectively optionally cyano-, fluorine-, methoxy- or ethoxy-substituted methyl, ethyl, n- or i-propyl, n-, i-, s- or t-butyl, acetyl, propionyl, n- or i-butyroyl, represents methoxycarbonyl, ethoxycarbonyl, n- or i-propoxycarbonyl, methylsulphonyl, ethylsulphonyl, n- or i-propylsulphonyl, represents propenyl, butenyl, propinyl or butinyl, $R^3$ represents hydrogen, represents cyano, nitro, fluorine, chlorine, bromine or represents respectively optionally fluorine-substituted methyl, ethyl, n- or i-propyl, $R^4$ represents hydrogen, represents respectively optionally fluorine-, chlorine-, cyano-, methoxy- or ethoxy-substituted methyl, ethyl, n- or i-propyl, n-, i-, s- or t-butyl, represents respectively optionally fluorine-, chlorine- or bromine-substituted propenyl, butenyl, propinyl or butinyl, represents methoxy, ethoxy, n- or i-propoxy or represents allyloxy, represents methylamino, ethylamino, n- or i-propylamino, n-, i-, s- or t-butylamino, dimethylamino or diethylamino, represents respectively optionally fluorine-, chlorine-, bromine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, or represents respectively optionally fluorine-, chlorine-, bromine-, cyano-, methyl-, trifluoromethyl- or methoxy-substituted benzyl or phenyl, and $R^5$ represents hydrogen, hydroxyl, mercapto, amino, fluorine, chlorine, bromine, represents respectively optionally fluorine-, chlorine-, cyano-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, represents respectively optionally cyano-, fluoro-, chloro- or bromine-substituted propenyl, butenyl, propinyl, butinyl, propenyloxy, butenyloxy, propinyloxy, butinyloxy, propenylthio, butenylthio, propinylthio, butinylthio, propenylamino, butenylamino, propinylamino or butinylamino, represents respectively optionally cyano-, fluorine-, chlorine-, bromine-, methyl- or ethyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl or cyclohexylmethyl, or represents respectively optionally cyano-, fluorine-, chlorine-, methyl-, trifluoromethyl-, methoxy- or methoxycarbonyl-substituted phenyl, phenoxy, phenylthio, phenylamino or benzyl.

3. A herbicidal composition comprising a herbicidally effective amount of a compound according to claim 1 and an inert carrier.

4. A method of combating unwanted vegetation which comprises administering to such vegetation or to a locus from which it is desired to exclude such vegetation a herbicidally effective amount of a compound according to claim 1.

* * * * *

UNITED STATES PATENT AND TRADEMARK OFFICE
CERTIFICATE OF CORRECTION

PATENT NO. : 6,200,934 B1  
DATED : March 13, 2001  
INVENTOR(S) : Klaus-Helmut Muller et al.

Page 1 of 1

It is certified that error appears in the above-identified patent and that said Letters Patent is hereby corrected as shown below:

Column 23,
Line 60, change "C3" to -- $C_3$ --

Signed and Sealed this

Eighth Day of July, 2003

JAMES E. ROGAN
*Director of the United States Patent and Trademark Office*